United States Patent
Martin et al.

(10) Patent No.: US 9,696,193 B2
(45) Date of Patent: Jul. 4, 2017

(54) REAL-TIME MEASUREMENT OF RESERVOIR FLUID PROPERTIES

(75) Inventors: Bradley Martin, Hameau Tilly (FR); Paul Guieze, Fontenailles (FR); David MacWilliam, Aberdeenshire (GB); Malcolm Atkinson, Aberdeenshire (GB); Bernard Theron, Gjovik (NO)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 1035 days.

(21) Appl. No.: 12/810,924

(22) PCT Filed: Dec. 24, 2008

(86) PCT No.: PCT/EP2008/011111
§ 371 (c)(1),
(2), (4) Date: Oct. 27, 2010

(87) PCT Pub. No.: WO2009/083243
PCT Pub. Date: Jul. 9, 2009

(65) Prior Publication Data
US 2011/0040501 A1    Feb. 17, 2011

(30) Foreign Application Priority Data
Dec. 27, 2007   (FR) .................................. 07 124102

(51) Int. Cl.
*G01F 1/00* (2006.01)
*G01F 1/74* (2006.01)
(Continued)

(52) U.S. Cl.
CPC ............... *G01F 1/74* (2013.01); *E21B 47/10* (2013.01); *G01N 9/00* (2013.01); *G01N 11/00* (2013.01)

(58) Field of Classification Search
CPC ....................................................... G01F 1/74
(Continued)

(56) References Cited

U.S. PATENT DOCUMENTS 5,689,540 A    11/1997  Stephenson
6,041,668 A     3/2000  Guieze et al.
(Continued)

FOREIGN PATENT DOCUMENTS

EP    1614465    1/2006
EP    1645863    7/2007
(Continued)

OTHER PUBLICATIONS

Extended Search Report issued in the related EP Application 07124102.0 dated Jul. 1, 2008 (6 pages).
(Continued)

*Primary Examiner* — Ricky Ngon
(74) *Attorney, Agent, or Firm* — Cameron R. Sneddon

(57) ABSTRACT

A system, method, and fluid analysis module are provided for the real-time analysis of multiphase fluids. The system generally comprises a sampling system for directing a fluid stream from a flow line to a fluid analysis module, a processor and communicator. The fluid analysis module comprises a sensor for measurement of at least one property of the fluid. The processor processes the measurement data from the sensor, and the communicator communicates the processed data to a central acquisition unit or computer.

35 Claims, 10 Drawing Sheets

(51) Int. Cl.
*E21B 47/10* (2012.01)
*G01N 9/00* (2006.01)
*G01N 11/00* (2006.01)

(58) Field of Classification Search
USPC ............... 702/6, 12, 22–26, 45; 73/1.02
See application file for complete search history.

(56) References Cited

U.S. PATENT DOCUMENTS

| | | | |
|---|---|---|---|
| 6,578,405 B2 | 6/2003 | Kleinberg et al. | |
| 6,758,090 B2 | 7/2004 | Bostrom et al. | |
| 7,384,453 B2 | 6/2008 | Bostrom et al. | |
| 7,474,969 B2 * | 1/2009 | Poulisse ................. | 702/45 |
| 7,523,647 B2 * | 4/2009 | Scott ..................... | 73/61.44 |
| 2002/0194907 A1 | 12/2002 | Bostrom et al. | |
| 2004/0010374 A1 | 1/2004 | Raghuraman et al. | |
| 2004/0129874 A1 | 7/2004 | Torgersen et al. | |
| 2004/0149634 A1 * | 8/2004 | Hughes ................... | 210/96.1 |
| 2004/0219064 A1 | 11/2004 | Raghuraman et al. | |
| 2005/0236155 A1 | 10/2005 | Killie et al. | |
| 2005/0279495 A1 | 12/2005 | Chen et al. | |
| 2006/0008382 A1 | 1/2006 | Salamitou et al. | |
| 2006/0008913 A1 | 1/2006 | Angelescu et al. | |
| 2006/0155474 A1 | 7/2006 | Venkataramanan et al. | |
| 2007/0041874 A1 * | 2/2007 | Sukavaneshvar ......... | B01F 7/26 422/68.1 |
| 2007/0061093 A1 | 3/2007 | Angelescu et al. | |
| 2007/0095528 A1 | 5/2007 | Ziauddin et al. | |
| 2007/0125233 A1 | 6/2007 | Bostrom et al. | |
| 2007/0143023 A1 | 6/2007 | Betancourt et al. | |
| 2007/0144268 A1 * | 6/2007 | Atkinson ............... | G01N 23/12 73/861.63 |
| 2007/0178595 A1 | 8/2007 | Raghuraman et al. | |
| 2008/0066904 A1 | 3/2008 | Van Hal et al. | |
| 2008/0105032 A1 | 5/2008 | Reddy et al. | |
| 2008/0121016 A1 | 5/2008 | Shah et al. | |
| 2008/0121017 A1 | 5/2008 | Shah et al. | |
| 2008/0135237 A1 | 6/2008 | Dubost et al. | |
| 2008/0141767 A1 | 6/2008 | Raghuraman et al. | |
| 2008/0148814 A1 | 6/2008 | Bostrom et al. | |
| 2009/0151426 A1 | 6/2009 | Shah et al. | |
| 2009/0158815 A1 | 6/2009 | Shah et al. | |
| 2009/0158820 A1 | 6/2009 | Bostrom et al. | |
| 2010/0145634 A1 | 6/2010 | Pinguet et al. | |

FOREIGN PATENT DOCUMENTS

| | | |
|---|---|---|
| EP | 1862781 | 12/2007 |
| EP | 1617202 | 9/2009 |
| GB | 2395555 | 5/2004 |
| GB | 2417913 | 3/2006 |
| GB | 2432425 | 5/2007 |
| GB | 2433273 | 6/2007 |
| GB | 2447908 | 6/2009 |
| WO | 01/98630 | 12/2001 |
| WO | 2005/031311 | 4/2005 |
| WO | 2006/037565 | 4/2006 |

OTHER PUBLICATIONS

International Search Report and the written Opinion issued in the related PCT application PCT/EP2008/011111, dated Mar. 5, 2009 (10 pages).

International Preliminary Report on patentability issued in the related PCT application PCT/EP2008/011111, dated Jun. 29, 2010 (7 pages).

* cited by examiner

REAL-TIME MEASUREMENT OF RESERVOIR FLUID PROPERTIES

CROSS-REFERENCE TO RELATED APPLICATIONS

The present application is based on and claims priority to EP Application No. 07124102.0, filed 27 Dec. 2007; and International Patent Application No. PCT/EP2008/011111, filed 24 Dec. 2008. The entire contents of each are herein incorporated by reference.

TECHNICAL FIELD

This invention relates to a system and method for real-time, fluid analysis of reservoir fluids during testing and/or production. In particular the present invention relates to analysing reservoir fluids at surface or subsea.

BACKGROUND ART

To evaluate and test underground formations surrounding a borehole it is often desirable to obtain samples of formation fluids for the purpose of characterizing the fluids.

Traditionally in most oilfield applications the hydrocarbon composition, trace elements and physical properties of reservoir fluids are measured at the surface adjacent the well using laboratory style instruments, analysers and equipment which may not necessarily be adapted to field measurements. Samples are also captured in sample receptacles and shipped to remote laboratories for further or more detailed analysis. Tools have been developed that allow samples to be taken from a formation in a logging run, during drilling, or well testing.

Though a fluid analysis on-site and in a continuous mode would offer many advantages generally it has not been possible to perform such analysis in a satisfactory manner before the present invention.

According to existing methods, samples for analysis are typically taken remotely in a sample receptacle, transported to the location where the analysis instrument lies and then the samples are introduced into an analyzer for analysis. A sample receptacle can be: a pressurized vessel such as a sample bottle, or a bladder or a balloon; and many other types well known in the art. Due to the time taken for manual sampling of fluid phases, and the time taken for analysis of these phases, the number of samples captured and the frequency, i.e. time between samples, the analysis of the fluid is limited.

Typically, pressure, temperature and flow rates are reported every 15 minutes during well clean-up and evaluation/production well testing operations. However samples and analysis are typically taken every 3 or more hours. This process is labor intensive and time consuming.

Furthermore during the clean-up and flowing of a well, the composition of the reservoir fluid changes with time. Initially the reservoir fluid will be contaminated with drilling and cushion fluids, perforation and formation debris, and injected chemicals. When the well is clean, hydrocarbon gas, oil and formation water will flow to surface. The quantity of each phase can change as the flow rate is altered and formation pressure is reduced.

It is common practice today during a well test, to take spot samples for analysis at the wellsite. The sampling frequency can vary between 1 to 5 hours. Sampling alone can take 1 hour and 3-4 hours for analysis. These results often do not show the true trend, whereby slugging or other well bore effects often give erratic results. With current methods it is not possible to measure frequently enough to plot the true trend.

In addition, bringing samples to the surface, transporting them to a laboratory, and separating the phase mixtures is time consuming, cost inefficient and provides only post factum-information. In addition fluid samples collected downhole can undergo various reversible and irreversible phase transitions between the point of collection and the point of laboratory analysis as pressure and temperatures change. Furthermore, from the time a sample is collected until it is analysed, there is potential for the sample to be contaminated from air or other external fluids, for the sample to react with the sample receptacle, for components in the sample to react among themselves, for the sample to degrade with time, or for loss of the sample due to leaks.

By directly measuring the properties of the fluid in the flow stream this will reduce impurities mixing with the sample, and the quality of results will be greatly improved as well as removing errors from contamination. In addition there is the Health, Safety and Environmental (HSE) benefit from reducing the exposure of personnel to reservoir fluids and high pressure.

One of the properties of the fluid which may be readily measured in the flow stream is the water liquid ratio (WLR) in a multiphase flow line (oil, water, gas) for a large range of flowing conditions. In particular, this is useful for high gas volume fraction (GVF), where GVF is greater than 95%. Particularly in these conditions, many existing methods for measuring the WLR which work on the flow rate are not successful due to the tiny volume of liquid to be split between the oil and water. Examples of known methods and apparatus for sampling a small sample of representative liquid before measuring the WLT and returning the sample to the line can be found in European patent application number EP1645863 entitled "A sampling apparatus" and PCT International publication number WO2006037565 entitled "A sampling apparatus." The document EP 1 614 465 describes a microfluidic system for performing fluid analysis having: (a) a submersible housing having a fluid analysis means and a power supply to provide power to said system; and (b) a substrate for receiving a fluid sample, having embedded therein a fluid sample inlet, a reagent inlet, a fluid sample outlet, and a mixing region in fluid communication with the fluid sample inlet, the reagent inlet, and the fluid sample outlet, and wherein the substrate includes a fluid drive means for moving the fluid sample through the substrate, and wherein the substrate interconnects with the housing. At least a portion of the fluid analysis means may be embedded in the substrate.

Further examples of known methods and apparatus for in-line multiphase flow meters which include gas-liquid separation technology and handle very high GVF multiphase flows can be found in United Kingdom patent number GB2447908 and PCT International publication number WO2005031311. In these further examples, however, the samples are taken in isokinetic conditions and this requires a complex control system which is not required in the current example.

The document GB 2417913 describes a microfluidic separator 110 comprising a porous membrane 108 supported by a microsieve. The membrane and sieve are arranged in parallel with the flow 106 of the multiphase mixture and the porous membrane is "wetted" by a portion of the mixture which is transmitted though the pores of the membrane for analysis. The membrane may be oleophobic and be arranged to transmit water based solutions or hydrophobic and arranged to transmit oil based solutions or both oleophobic and hydrophobic and arranged to transmit gases. Pressure across the membrane is maintained below capillary breakthrough values for the non-wetting phase and the flow rate though is significantly less than that passing over the membrane thus reducing problems related to cake build up and fouling. The separator may be integral to or connected to a microfluidic sample manipulation/analysis chip and one or several valves, possibly in conjunction with a micropump, which may be used to maintain the pressure drop below the non-wetting phase breakthrough pressure. Collection channels may also comprise an H-fractal configuration. The main application described relates to the use of the separator in logging while drilling (LWD) or measurement while drilling (MWD) to provide continuous real-time data concerning fluid in a subterranean formation.

The document GB 2 433 273 describes a method for determining a property of formations surrounding an earth borehole being drilled with a drill bit (15) at the end of a drill string, using drilling fluid that flows downward through the drill string, exits through the drill bit, and returns toward the earth's surface in die annulus between the drill string and the periphery of the borehole. The method includes the following steps: obtaining, downhole near the drill bit, a pre-bit sample (211) of the mud in the drill string as it approaches the drill bit; obtaining, downhole near the drill bit, a post-bit sample (212) of the mud in the annulus, entrained with drilled earth formation, after its egression from the drill bit; implementing pre-bit measurements on the pre-bit sample; implementing post-bit measurements on the post-bit sample; and determining a property of the formations from the post-bit measurements and the pre-bit. The measurements may be completed downhole, for example using a mass spectrometer.

The application of the present invention to measure WLR fluid property has the advantage of a small sample of representative liquid from the flow line being used and then being returned to the flow line. This application further overcomes the difficulty in making the WLR measurement itself because of the differences in physical properties of the oil and water in standard flow lines by the measurement made in a very small or mini-channel where the superficial tension maintains both phases at the same speed.

DISCLOSURE OF THE INVENTION

Accordingly a first aspect of the present invention relates to a system for the real time analysis of a fluid stream from a flow line comprising: means for directing a fluid stream from a flow line to a fluid analysis module located outside the flow line; a fluid analysis module comprising a sensor for measuring at least one property of the fluid; a processor for processing the measurement data from the sensor; and communication means for communicating the processed data to an acquisition unit or a computer.

The system may contain a separation module for separating the phases of the multiphase fluid stream. In an alternative embodiment the fluid stream may be taken downstream of an existing separator device in which case there will be no need for a separation module. The system may also include a pretreatment module for removing contaminants from the fluid stream. The fluid analysis module can comprise an array of sensors for measuring at least one property of the fluid. The sensor of the fluid analysis module can be configured for measuring properties of separated water, oil and/or gas phases of a multiphase fluid.

Each sensor comprises a sensing means for analyzing at least one fluid property. The processor can be part of the fluid analysis module or alternatively the processor can be part of the data acquisition module. In one embodiment the sensors comprises the processor for processing the data collected from the sensor and communication means for communicating the processed data to a central acquisition unit or computer for further processing.

Alternatively, each sensor comprises the sensing means, while the processor can process the data from a plurality of sensors and the communication means is also common to a plurality of sensors. Yet another possible arrangement includes the sensor having sensing means and comprises a processor for processing the data collected from the sensor, with the communication means being common between a plurality sensors and as such communicating processed data from a plurality of sensors.

The communication means may typically comprise a data acquisition module to gather the data generated by each sensor after it has been processed by said processor. It may also have a computer system configured to further process the gathered data to generate real-time analysis such as providing data on a physical property of the fluid reservoir in real time.

The system may also comprises a post-treatment module connected downstream of the fluid analysis module to prepare the sample for disposal. A fluid sample outlet is connected to the fluid analysis module to discharge the fluid sample. The fluid sample outlet can be in fluid communication with a storage chamber or with the flow line.

In another aspect of the present invention the fluid analysis module may comprise a fluid sampling device in communication with the flow line, a gas-liquid separator for separating gas from liquids being in communication with the fluid sampling device, and a water to liquid ratio measurement device being in communication with the gas-liquid separator by means of a conduit having a diameter equal to or less than 3 millimeters. The fluid sampling device may be used to return a fluid sample to the flow line.

Preferably the system is for the analysis of reservoir fluids from a well.

The present invention system and method are especially suitable for measuring fluid characteristics on the surface or subsea.

Another aspect of the present invention provides a method for the real time analysis of a multiphase fluid, the method comprising directing a sampling stream of a fluid externally from a flow line; directing individual phases of a fluid stream to a fluid analysis module comprising an array of sensors; measuring a property of the sampling fluid stream using a sensor; and processing the measurement.

The method may further comprise gathering processed data from the sensor and further processing the gathered data generating real-time fluid property analysis. The analysis may then be transmitted from the site where the analysis takes place to any desirable remote location.

The fluid analysis module can comprise an array of sensors, each sensor measuring at least one property of the fluid.

In one embodiment the method comprises separating the phases of the multiphase fluid into single phase sample streams after obtaining the fluid from the flow line. Alternatively the method can comprise separating the phases of the multiphase fluid into single phase sample streams before obtaining the fluid from the flow line.

The method can further comprise removing contaminants from the fluid sample. The fluid sample can be discharged back into the flow line after measuring a property of the fluid. Chemical agents may be used to measure a property of the fluid. These chemical agents may then be separated from the sampled stream before discharging the sampled stream back into the flow line or a container as the case may be for later treatment or disposal.

Also, the method may comprise storing a sample for further analysis off-line in addition to the real time analysis.

In a further form of the present invention the fluid analysis module may comprise a fluid sampling device in communication with the flow line; a gas-liquid separator for separating gas from liquids being in communication with the fluid sampling device; and a water to liquid ratio measurement device being in communication with the gas-liquid separator by means of a conduit having a diameter equal to or less than 3 millimeters.

The method if preferably for to measuring fluid properties of any fluid emanating from a hydrocarbon reservoir either during the exploration, testing or production stage of the well. When the system is deployed in a subsea environment the analysis may be transmitted to a surface data acquisition module using wire or wireless communications.

Preferably the method uses the system described above.

Further according to the present invention there is provided a fluid sampling device in communication with a flow line; a gas-liquid separator for separating gas from liquids being in communication with the fluid sampling device; and a water to liquid ratio measurement device being in communication with the gas-liquid separator by means of a conduit having a diameter equal to or less than 3 millimeters. The fluid sampling device may be used to return a fluid sample to the flow line.

According to another aspect of the present invention there is provided a method for the real-time analysis of the water to liquid ratio of a multiphase fluid, the method comprising: obtaining a fluid sample from a multiphase fluid flow line; passing the fluid sample through a liquid-gas separator and separating the gas from the liquid in the sample; passing the separated liquid through a conduit which connects the liquid-gas separator to a water to liquid measurement device, the conduit having a diameter equal to or less than 3 millimeters; and measuring the water to liquid ratio by means of the water to liquid measurement device. The method may further comprise returning the fluid sample to the flow line.

The present invention system and method overcomes some of the drawbacks of existing systems and methods, allowing for continuous fluid property analysis of reservoir fluids on site. Some of the advantages of the present invention system and method are briefly described as follows.

It allows for real time measurements of fluid properties. This is particularly advantageous in situations where the fluid property changes over time. This is, to a varying extent, the situation with measurements of the pH of water, the $H_2S$ concentration in gas, Hg in gas, and radon in gas.

It further allows collection of the data and use of the data on a continuous basis allowing decisions to be made on a real time basis. Such decisions are of particular importance in making decisions during well test, clean-up operations or well production. It also eliminates the long delays in the shipping of samples to laboratories required by existing techniques.

The present invention is less costly and more efficient than existing methods. It also eliminates handling of hazardous, and/or pressurized samples thus improving the overall safety of the fluid analysis.

The data analysis from the present invention system can be readily used in many applications such as:
Prevention of corrosion and scale
Analysis of environmental impact
Determining sales gas quality
Catalytic poisoning
Characterizing and modeling reservoir fluid properties
Designing of production and processing facilities
Time dependent analysis—decaying elements (Radon) and sulfur species
Varying concentrations versus time due to thermodynamic conditions changes.
Safety Monitoring and Analysis
Well Test Optimization These and other advantages will become apparent to persons skilled in this art from the following detailed description of various embodiments of the present invention in conjunction with the following drawings. These embodiments are provided by way of example only and should not be construed as unduly restricting the scope of the present invention which is described in the appended claims.

MODE(S) FOR CARRYING OUT THE INVENTION

Figure 1:
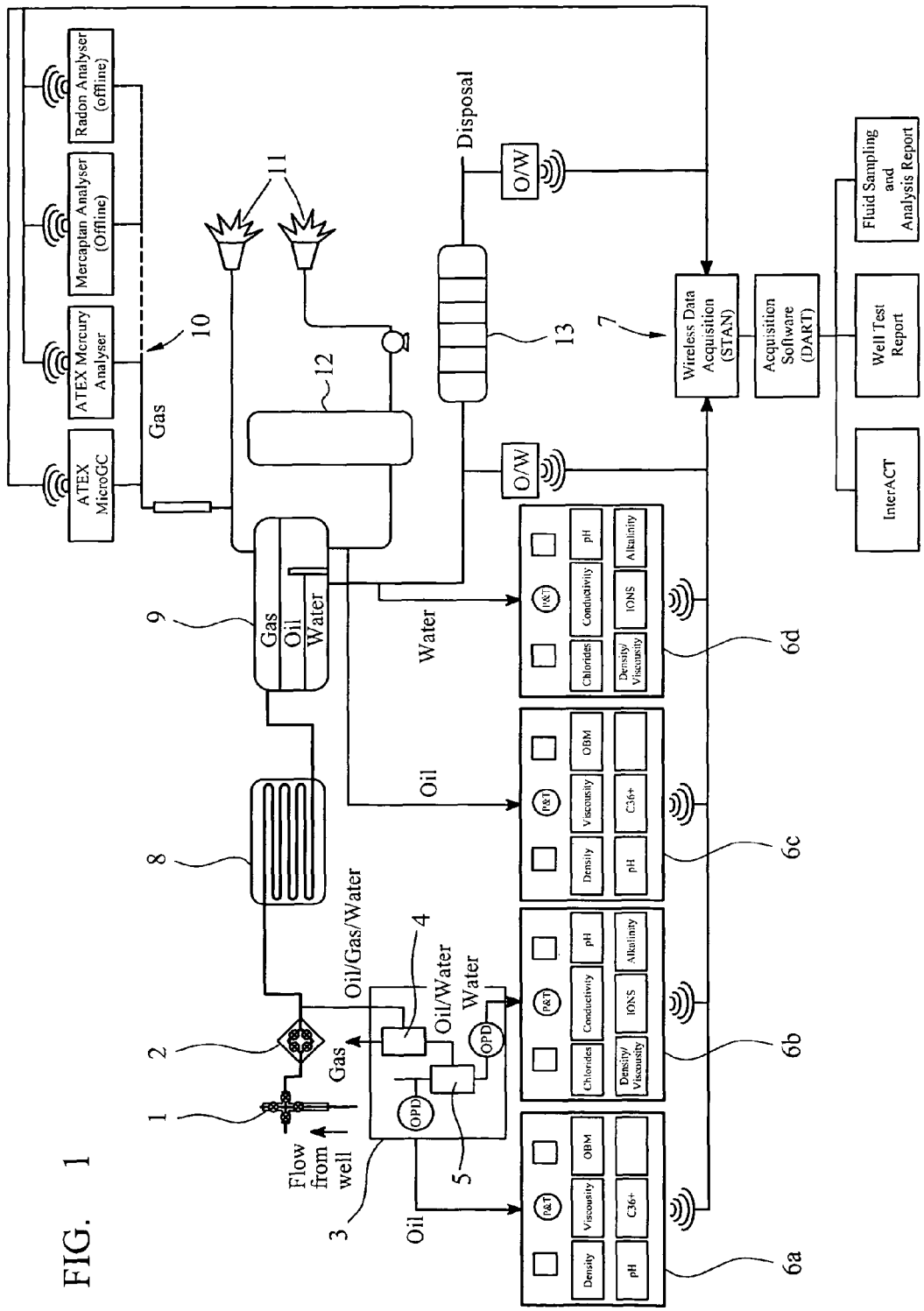
FIG. 1 is a schematic diagram of the system according to one embodiment of the present invention.

It is desirable to provide a system that can directly measure properties of a fluid in a flow line and provide real-time analysis of the results. FIG. 1 shows a schematic drawing of the present invention capable of measuring properties of a fluid in a flow line and providing real-time analysis of the results. The system is described with reference to analysing fluid from a well and includes a sampling module for obtaining a portion of fluid from a well, a pretreatment module, fluid analysis module comprising a sensor array, a post treatment module and a data acquisition module. Fluid flow from a well is diverted into the system located externally from the well flow line at the flowhead (1) position. A choke manifold (2) controls the flow of the fluid sample stream out of the well flow line and into the system.

The fluid is then directed to a pretreatment module (3). There the multiphase fluid from the well is separated into single phases. A first gas/liquid separator (4) separates the gas from the oil/water, a second oil/water separator (5) separates the oil and water into single phases. The pre-treatment module can also comprise a unit to remove any solids or impurities that would negatively affect the measurement. Each single phase is directed into a sensor assembly (6a, 6b). Each sensor assembly can comprises multiple sensors for measuring different properties of the fluid for example, pressure and temperature, density, viscosity.

The measured data from each of the sensor assemblies is communicated to a data acquisition system (7) for further processing to provide real-time analysis of the fluid flow in a well. This processed data can then be transmitted to a remote location.

In a conventional well test configuration a fluid sample is diverted from the flow line and flowed through a heat exchanger (8) and a three phase separator (9) which separates the multiphase fluid into a gas phase, liquid, and water phase. A sample of the gas phase is directed to a series of gas analysis units (10). These units may be online or offline. The remaining portion of the gas sample is burnt off by burners (11). A sample of the oil phase and a sample of the water phase are directed to sensor assemblies (6c, 6d) where properties of the oil and water are measured. The remaining portion of the oil is diverted to a tank (12) for storage and to burners (11). The remaining water is directed to a water treatment unit (13) for eventual disposal. The measured data from the online sensors is communicated to a data acquisition module (7) for further processing.

The system can be used during exploration, evaluation, production, extended or cleanup well tests. The system may be used for permanent installation, temporary installation or as a portable unit. The configuration of the system will depend on the use of the sensor and the fluid being analysed. The modules may be connected as a multi sensor module configuration as shown in FIGS. 2 and 3 or as individual sensors for direct measurement of the flow line (FIG. 5).

Figure 2:
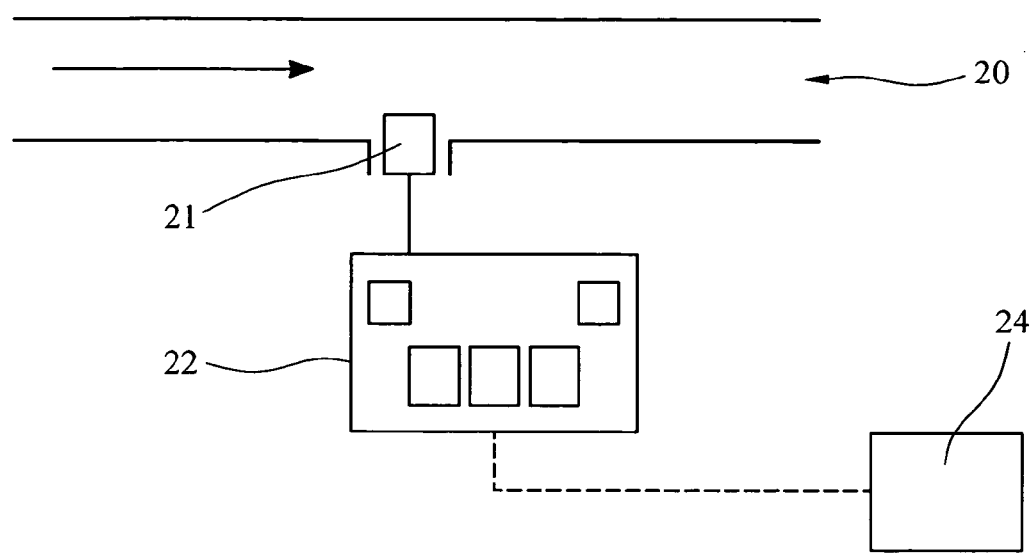
FIGS. 2 and 3 show a schematic diagram of a multi-sensor embodiment of the present invention
Figure 3:
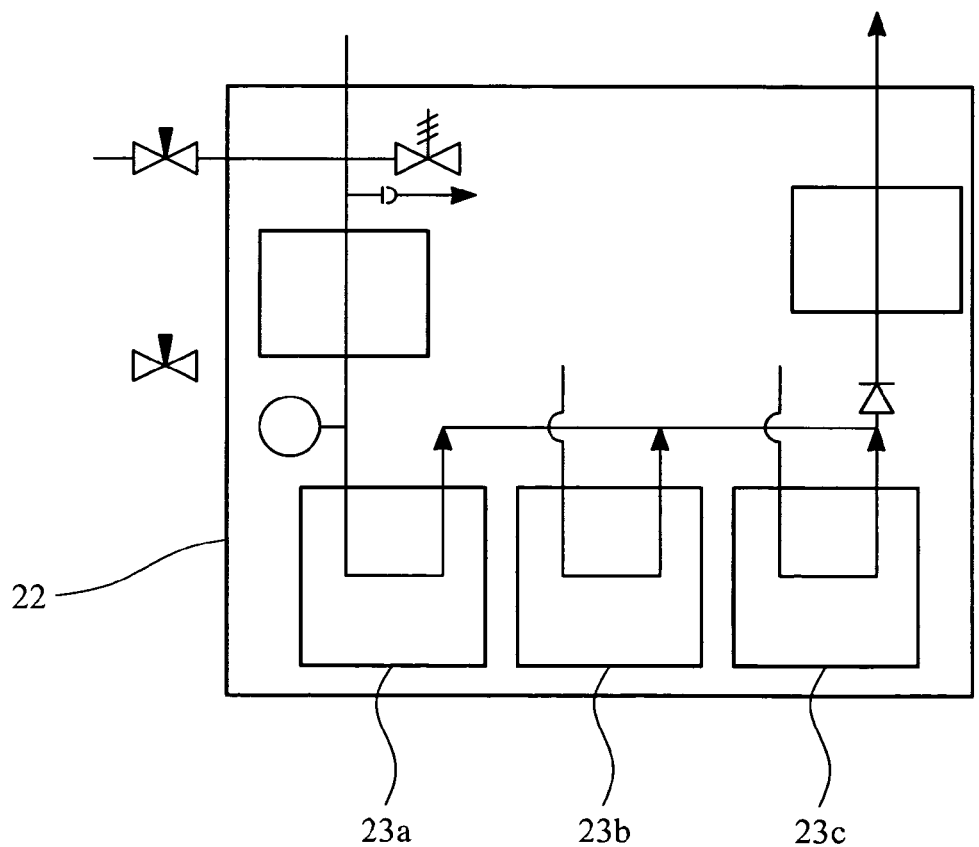

With reference to FIGS. 2 and 3 the system is shown to be installed in fluid communication with a main flow line (20). A sampling unit (21) diverts a fluid stream from the main flow line (20) into the sensor system (22) located external from the main flow line. The sampling system (21) may also comprise a pre-treatment module which can include a filtering system to remove contaminants from the sample fluid and a separation system to separate the multiphase fluid into single phases. The sampling system (21) is connected to the sensor system (22) where a property of the fluid is measured and processed, via a sampling port. The sampling port can consist of a valve for flow regulation. The sensor system can comprise an array of sensors (23a-c). The sensor will vary depending on the fluid being analysed and are described in further detail below. After the sample fluid has been analysed the fluid is directed away from the sensors to a post treatment module for disposal. The measured data can then be communicated to a data acquisition unit (24) where the data is processed generating real-time analysis. This data can then be transmitted from the site of analysis to any remote location.

Figure 4:
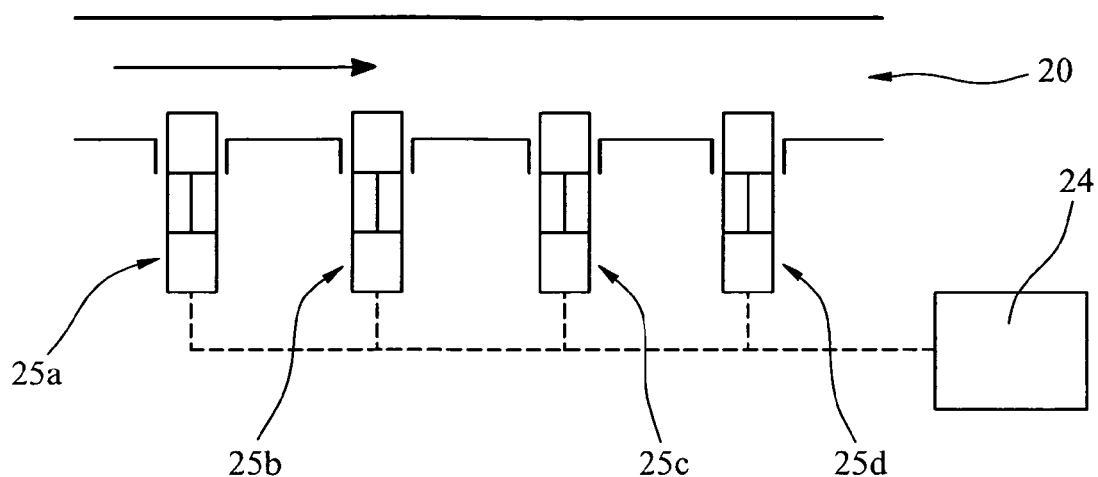
FIG. 4 is a schematic diagram showing details of one embodiment of the present invention.
Figure 5:
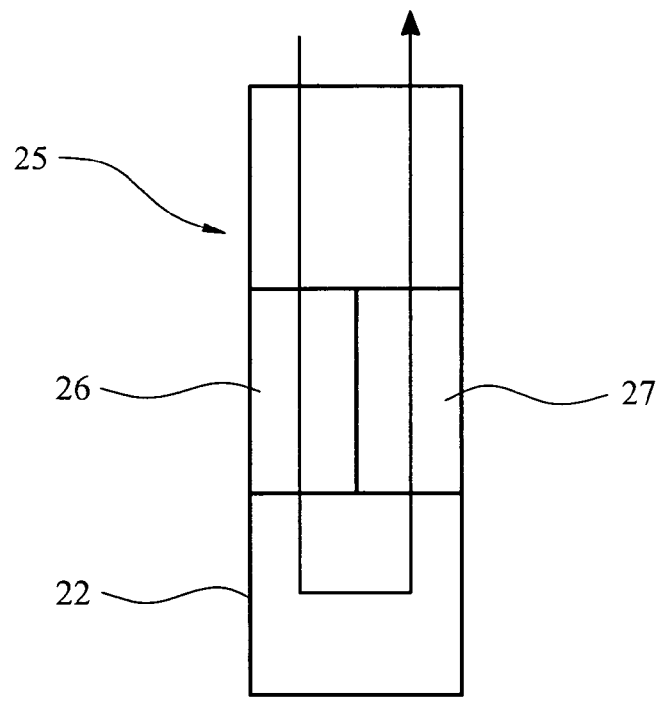
FIGS. 5 to 7 show schematics showing details of different configurations of the present invention.

The inline sensor assembly (25), as shown in FIG. 5, can be installed in fluid communication with the flow line (20) for direct measurement of the fluid properties of a fluid. Fluid flows through the sensor module (22) via a pre-treatment module (26) where a property of the fluid is measured from the main flowline, before flowing back out the system via a post-treatment module (27). With reference to FIG. 4 a multiple array of inline sensor assemblies (25a-d) can be used with each sensor in fluid communication with the main flow line (20). A sample of fluid flows out of the main flow line (20) and through each sensors module where a property of the fluid is measured. The measurement data from each sensor module can then be communicated to a central data acquisition unit (24) where the data from all the sensors is processed generating real-time analysis. This data can then be transmitted from the site of analysis to any remote location.

Figure 6:
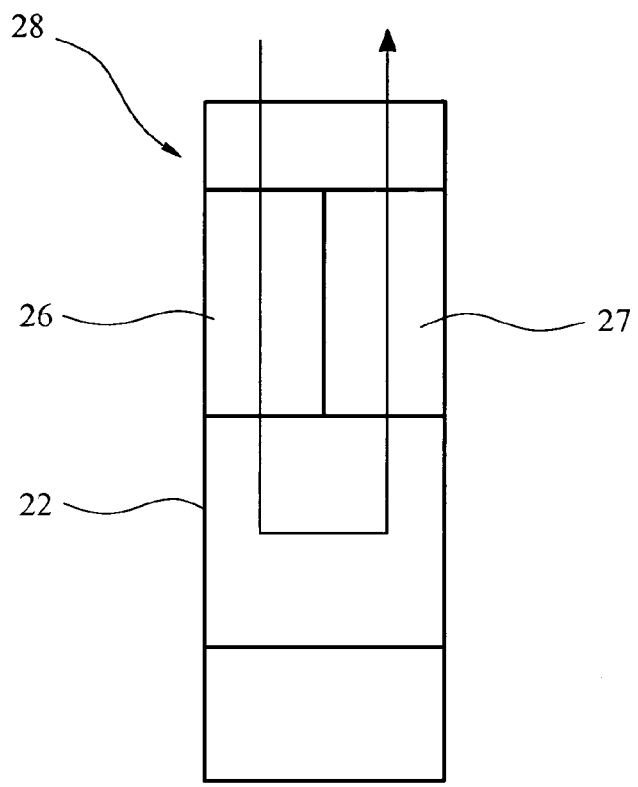
Figure 7:
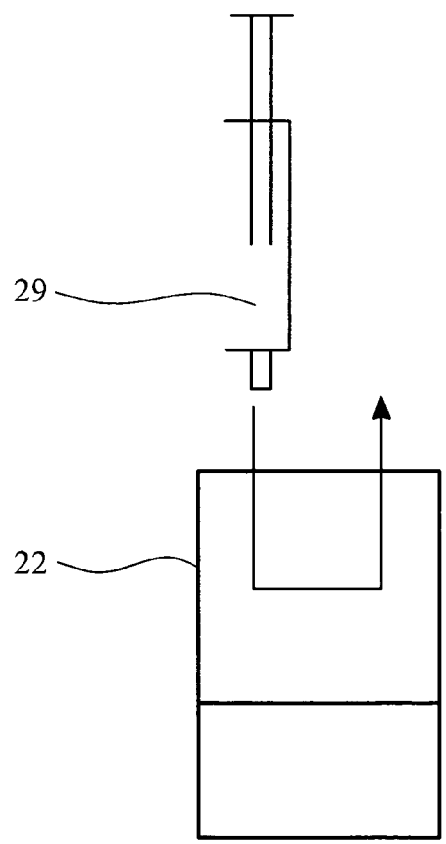

Alternatively, the system is configured as a handheld HP sensor assembly (FIG. 6). The handheld sensor assembly (28) is configured to be connected to an existing sampling port where fluid can enter the system (28) via a pretreatment module (26) and a property of the fluid measured by the sensor assembly (22) before fluid flows back out via a post treatment module (27). The handheld sensor assembly can also be configured to be connected to bottomhole sampling tools, sample bottles, PVT cells or any other high pressure (HP) source. The system can also be configured to be used with the manual injection of a fluid using a disposable syringe (29), gas bag or connection to any low atmospheric pressure sample source, to deliver a sample fluid stream to the sensor system (22) as shown in FIG. 7.

A portion of the fluid from the flow line will be diverted into the system for analysis. Samples will be captured from single or multiphase fluid streams using single or multiple sampling probes that selectively sample the required phase. The probe may be fixed or have the ability to move and be located at any point across the sample stream. The probe may incorporate pressure regulation. The location of the sample collector will depend on the purpose of analysis. The system can be connected to take samples from wellhead/flow head, upstream/downstream choke manifold, upstream/downstream or directly from multiphase flow meters (i.e. PhaseTester), separator effluent inlet/outlet streams (gas, oil, water)/direct, Surge/Gauge/Atmospheric tanks, effluent outlets, inlet and outlet of other well testing vessels (e.g. water treatment unit, heaters, sand filter etc).

During a multiphase well test, clean-up or production test, no phase separation occurs and all samples are taken from a multiphase stream. In this situation the sampling probe can be located upstream or downstream of the choke manifold, upstream/downstream of the multiphase meter or directly from the multiphase meter.

The system has the advantage of supplying chemical and physical properties of the phases at flow line conditions and in real time which can then be used to improve the calculation of phase flow rates. Currently fluid properties (density, viscosity) are measured at ambient conditions and calculated at line conditions using Equation of State type calculations. After the sample of fluid has separated from the main flow line, the sample is treated before undergoing analysis. The pretreatment module allows for sample separation and filtration for the removal of sand/solids with a particulate filter/screen, for the separation of liquid from gas or gas from liquid with a membrane filter, or for the separation of oil from water or water from oil with a membrane filter. Alternatively the pretreatment module can comprise a cyclone, centrifugal separator, or gravity separator to separate and filter particles from the sample. Filters and membranes may be used in series and may be of different grades to increase the purity of the sample phase. The module may also comprise pressure relief valves and/or rupture discs and pressure and temperature gauges, sensors and/or transducer to regulate the sample pressure and flow.

Once the sample fluid has been analysed the fluid will be directed to the sensor array. There may also be a connection to a sample receptacle which can store a sample of the fluid for analysis in an onsite laboratory or shipping to a laboratory at later stage. In another embodiment any analytical instrument capable of measuring the desired property can be used as a sensor in the array.

The sensor array includes pipe work and manifolds to connect from the sample pretreatment module to each sensor and each sensor to the sample post-treatment and disposal module. A sampling port from the pretreatment module can consist of a valve for flow regulation and a port with threaded connection. Each sensor port will include check/non return valves that so when removed the system will hold pressure and flow is not interrupted. Each sensor can act independently although the value obtained by one sensor can be used to calculate or correct values obtained from other sensors, e.g. density from a DV-rod can be used to calculate viscosity from Vibrating wire. The number of sensors is not limited and will depend on the situation.

The system may comprise a plurality of sensors depending on the fluid characteristics to be measured. For instance the system may include one or more physical or chemical sensors for measuring inter alia any of the following:

For the Water Phase
Water conductivity/resistivity
pH
Alkalinity
Density (DV Rod, Vibrating Wire)
Viscosity (DV rod, Vibrating Wire)
Ions (Cl, Ca, Mg, Nitrate)
Sulphate Reducing Bacteria
Turbidity
Scaling
$H_2S$
$CO_2$
For the Oil Phase
Density (DV rod, Vibrating Wire)
Viscosity (DV rod, Vibrating Wire)
OBM (oil based mud) contamination (DFA, GC)
BS&W (basic, sediment and water) (Optics)
Composition (C1-C36+) (Downhole MicroGC)
Wax content and deposition pressure
Asphaltene content and deposition pressure
$H_2S$
For the Gas Phase
Composition (C1-C12+, $O_2$, $N_2$, $CO_2$, $H_2S$, $H_2O$)
$H_2S$
Mercury
Radon
Mercaptans (C1-C6 R—SH, COS, $CS_2$)
$CO_2$ The sensors may be packaged into a single unit in the fluid analysis module or as individual sensors connected directly to the sample source with a common acquisition unit and software.

Figure 8:
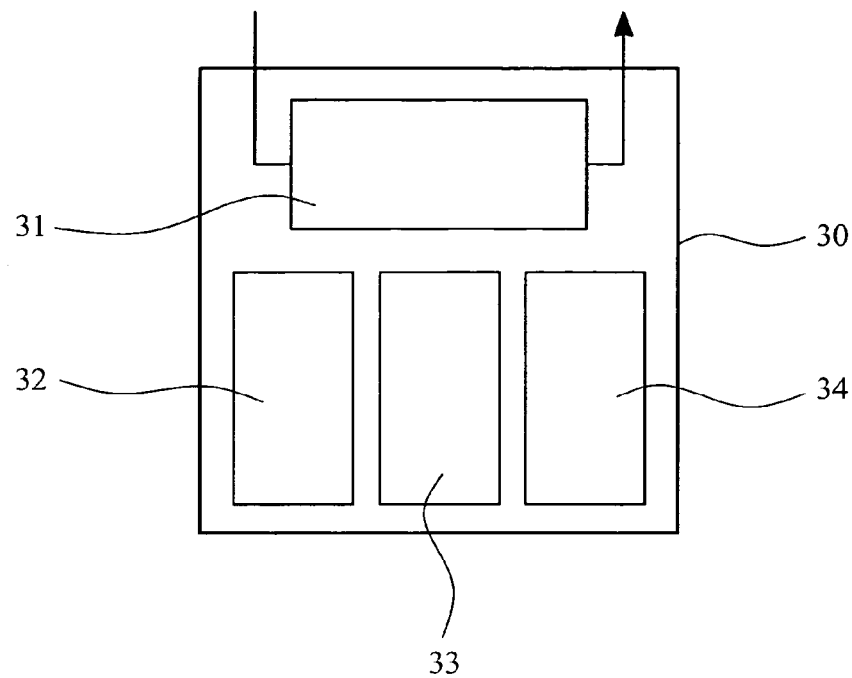
FIG. 8 is a schematic diagram of a sensor that can be used in the present invention.

As shown in FIG. 8 each sensor (30) will consist of four main sections, a measurement section (31), an electronics section (32), a communication section (33) and a power section (34). The measurement and electronics sections for each sensor may differ between sensors of the array as they will depend on the physical or chemical property that the sensor is measuring and the processing required to produce the measured property.

Each sensor can perform onboard calculations of the measured property and thus have calibration coefficients stored on the sensor. In this way each sensor is independent and not reliant on the data acquisition module or software. The communication module of the sensor allows each sensor to communicate independently between the sensor and data acquisition module and between the sensors themselves. Each sensor can have an independent power supply, such as an onboard battery to enable operation in a wireless mode or as a hand held sensor. They can also be supplied power from an electrical cable or power converted from an optic fiber cable from the surface. It is preferred that the electric connections and the communication modules are the same across each sensor in the array.

Various sensors e.g. pH, alkalinity, ion, may introduce chemicals, reagents or dyes into the sample stream during the analysis process. Therefore the system can further comprise a post treatment system. Each sensor is in fluid communication with the post-treatment. The post treatment system can incorporate scrubbers, for example activated carbon, filters/membranes, centrifugal, cyclone and/or gravity separators to remove all chemicals from the sample that have been added during the analysis process to return the sample to its original state before analysis prior to discharging the sample back into the flow or into a storage vessel.

Figure 9:
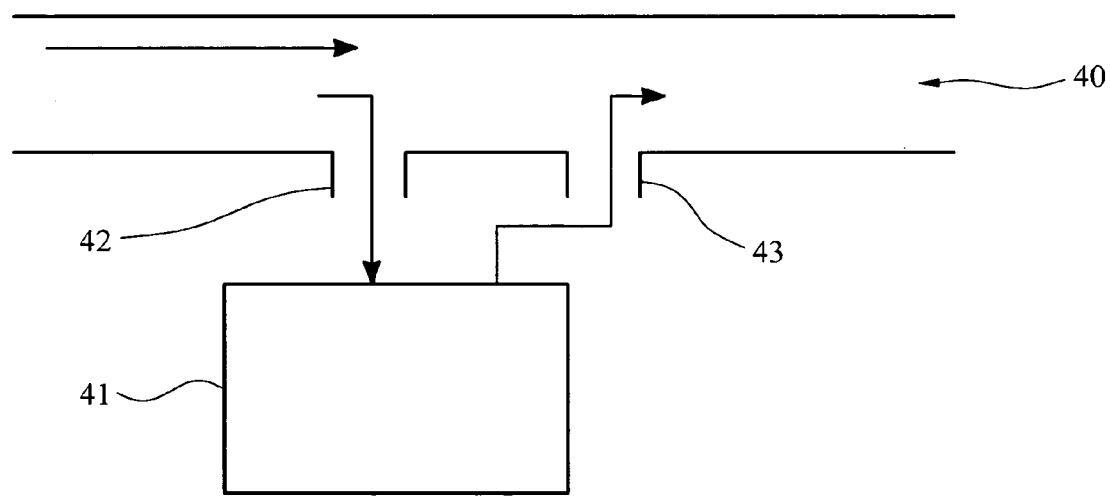
FIGS. 9 to 11 show schematic diagrams showing details of different configurations of the post treatment module of the present invention.
Figure 10:
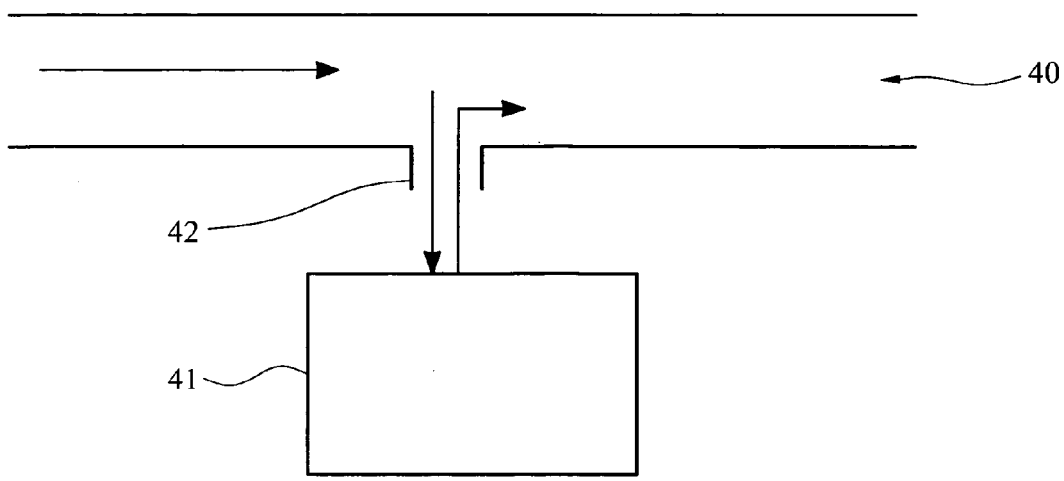

The sample disposal system can include a high pressure pump to inject the sample into the flow line. As shown in FIG. 10 the fluid sampling stream can be injected back into the main flow line (40) after analysis by the system (41) at the original sampling point (42). In another embodiment of the present invention a fluid sample stream is directed into the system from a fluid inlet (42) and then injected back into the main flow line (40) from the system after analysis via an outlet (43) downstream of the original sampling point as shown in FIG. 9.

Figure 11:
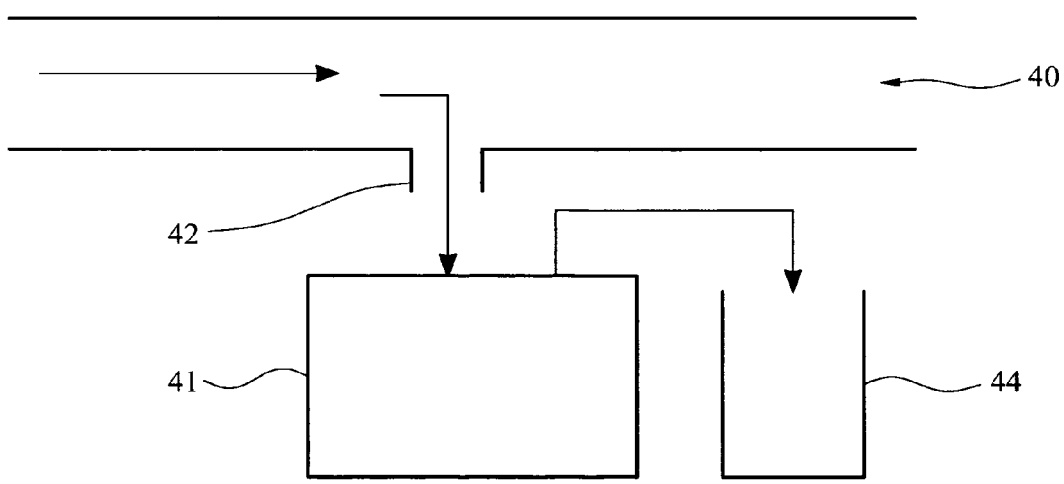

In another embodiment of the present invention, as shown in FIG. 11, if it is not possible to sufficiently remove from the fluid sample, the introduced chemicals etc used during the analysis process such that the sample fluid can be injected back into the main flowline (40), the sensor module (41) can be connected to a waste vessel (44) or tank in which the sample can be stored for later disposal.

Measured sensor data can be handled in several ways. The raw data obtained by the sensor can be processed by a processor located on the sensor with the processed value sent to the data acquisition system. Calibration coefficients and calculations will be stored in the sensor electronics to enable the data to be processed. Alternatively the raw data obtained by the sensor is sent to the data acquisition system and processed by a processor of the data acquisition system whereby the calibration coefficients and calculations will be stored in the data acquisition system.

If not processed by the data acquisition module the processed data is transmitted to the data acquisition module. Communication from the sensor to the data acquisition system can be via electrical cable, optical fibre or wireless i.e. Wi-Fi, blue tooth, radio, and infrared. The type of communication used depends on the site/location of the system. At the data acquisition module the process fluid property and chemical data obtained can be used in conjunction with pressure, temperature and flow rate measurements, if required, to:

Monitor clean-up of drilling and completion fluids (e.g. OBM, WBM)
Monitor the change in trace elements such a $H_2S$, mercury and radon which are scavenged by steel tubulars, valves, vessels, etc
Improve the accuracy of flow-rate calculations
Monitor effect of chemical injection Monitor the change in compositions due to changes in flow rates or conditions Predict/Monitor Hydrate formation Predict/Monitor Asphaltene precipitation This system has the benefits of optimising the clean-up, main flow and shut in periods, by lengthening the clean-up periods to allow the well to clean-up fully and shortening clean-up flow periods once the well is suitably clean. It allows sampling for lab analysis at the optimum time, for example, sampling after the well is clean and when composition is stable or at equilibrium, eliminates the need of extra sampling flow period and can be used for surface and bottomhole samples. The system also allows the flow rate versus choke setting to be optimised. This is critical on gas condensate wells where liquid is accumulating in the well bore and slugging. It ensures the fluid property data delivered at the wellsite is representative.

The data acquisition module comprises a computer system configured to further process and analysis the data about the fluid to allow for real time trending, well test optimization and well control. Data from the multiple sensors is received by the single data acquisition system and processed using a single computer program to allow real-time trending, well test optimization and well control. The computer system can:

Display numerically and graphically the measured values—instantaneous readings and historical trends.

Have multiple sensors plotted on the same display in addition to pressure, temperature and flow rates.

Log/store historical data

Generate a report

Export data (ascii, xls etc)

Allow well test control/production optimization

Trigger alarms (high/low level—e.g. $H_2S$ above 10 ppm)

Interpret and model the data

Predict clean-up time

Allow hydrate prediction based on water and gas composition (water and GC measurements required)

Allow flow assurance predictions (wax, Asphaltens and scale)

PVT property predictions (EOS/ANN based on certain measured properties)

Inorganic Solids deposition (Scale)—based on correlation/prediction software

Data may also be fed into well testing data acquisition software for monitoring fluid property trends in relation to changes in flow/pressure and temperature conditions.

The data acquisition module can comprises communication means to transmit the analysis obtained from downhole to the well site surface. From the well site the data can be transmitted by a wellsite user worldwide via a satellite.

The system can be connected to bottomhole sampling tools used in open hole, cased hole and production. This may be a direct connection or inline during sample transfer.

Alternatively, it can be connected to a pressurised sample bottle containing samples transferred from bottomhole sampling tools or captured at surface from the wellhead/upstream choke manifold, separator or MFPM. It can be used at the wellsite, mobile lab at the wellsite, remote lab, PVT Labs or any another analytical laboratory. The system can also be used to analyse samples at low or atmospheric pressure.

Figure 12:
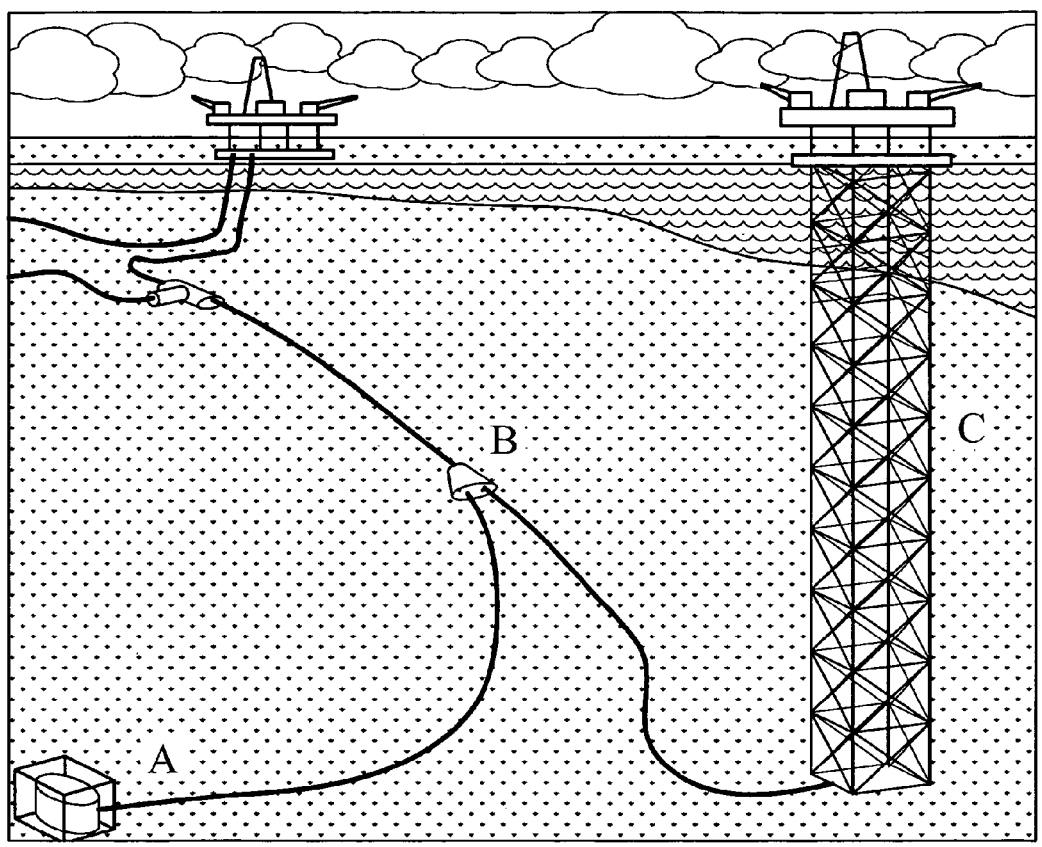
FIG. 12 shows one application of the present invention in the oilfield area.

The system can be used in surface or subsea applications for monitoring fluid properties during production from the wellhead to the process facility. In subsea application, as shown in FIG. 12, the system can be located at a position (A) downstream of a subsea well head where properties of an individual well can be monitored. Alternatively where fluid from two wells is mixed the system can be located at a position (B) after fluid from two wells is mixed. The fluid properties of the co-mingled fluid can be measured at this point and compared to the individual well properties. In another embodiment the system is located at a position (C) on the riser between the sea floor and platform to monitor changes to the fluid properties as the sample encounters different conditions e.g. reduction in temperature and pressure. The system can be used upstream, downstream or directly from a subsea multi-phase meter.

Fluid properties measured at locations A, B and C are used for flow assurance and solid deposition monitoring. The fluid properties are fed into simulation software for the prediction of flow rates, hydrate formation, organic solids deposition (Wax and Asphaltene) and inorganic deposit (Scale). The performance of gas injection, chemical injection and pipeline heating can be monitored and adjusted based on the change in fluid properties e.g. monitoring fluid density during gas lift operations.

In surface applications, the system can be located/samples taken from the equivalent locations i.e. wellhead, co-mingling/mixing points.

The system can also be used on production facilities to monitor to chemical and physical properties. The sensor manifold or multiple sensors are connected directly into the flow line, are permanently installed or installed on a short term basis. Typical applications are measuring fluid properties from individual wells prior to mixing, measuring fluid properties at each stage of separation (before, intermediate and after), before and after treatment vessels i.e. mercury scrubber, $H_2S/CO_2$ separation, and measuring fluid properties during well clean-up for new or work over wells.

Figure 13:
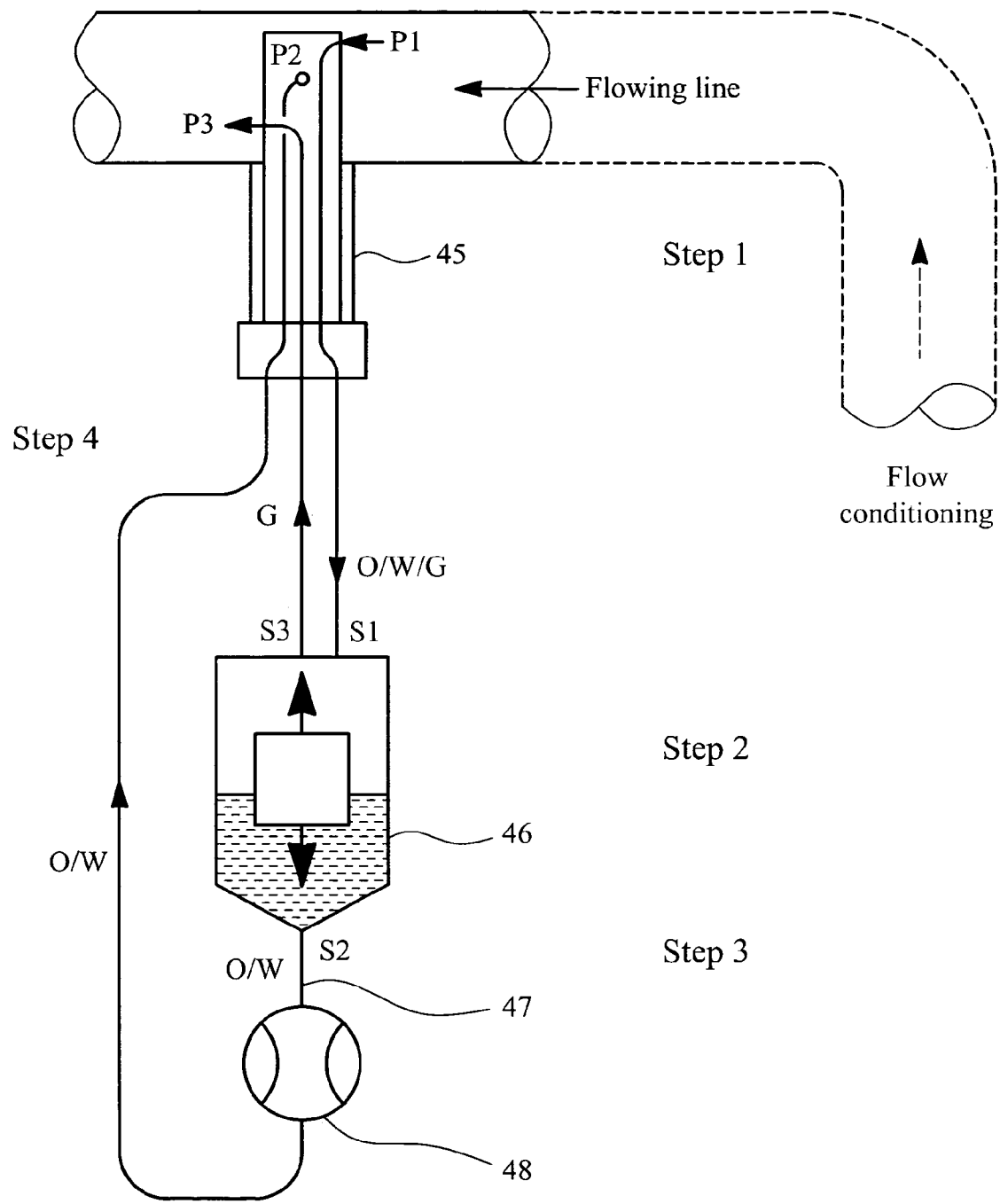
FIG. 13 shows a schematic diagram of a fluid analysis module according to one embodiment of the present invention.

In a further embodiment of the present invention the fluid analysis module of the system may be configured as shown in FIG. 13. In FIG. 13 the fluid analysis module may comprise a sampling probe (45), a self regulated mini separator (46), a mini channel (47) and a water liquid ratio (WLR) measurement device (48). The fluid analysis module of FIG. 13 provides a method for measuring the WLR in a multiphase flow line with oil, water and gas for a large range of flowing conditions and particularly in high gas volume fraction (GVF), where GVF is greater than 95%. Production management of an oil field must cope with large quantities of produced water and therefore must know the source of the water. There are several known methods used for measuring the WLR but they are challenged when the GVF in the production line becomes high. The reason for this is that at high GVF, the WLR measurement are made on a tiny amount of liquid immersed in a large volume of gas, typically 1% of liquid dispersed in 99% of gas.

One option is to get a sample of liquid representative of the WLR. It has been observed that the oil and water are well mixed when flowing in multiphase flow after the pipe direction changes from horizontal to vertical. The presence of gas in the multiphase flow further largely enhances the mixing of the oil and the water after the direction changes. The fluid analysis module of this embodiment takes advantage of this physical behavior to get a representative sample of liquid to perform the measurement.

The fluid analysis module of FIG. 3 may be used according to a method which comprises a number of steps. There are preferably four steps as indicated in FIG. 13. Step 1 comprises taking a spot sample by the sampling probe 45. The spot sample is taken in a conditioned flow, that is, in at least a section of vertical ascending flow upstream of the sampling probe 45. The sample is taken at the correct location which is where the spot sampling probe 45 is preferably located after the pipe direction changes and is facing the flow. Usually the relative volume of the three phases in the sample is not representative of the flow in the line and there is an excess of liquid. However, due to the good mixing of the liquid in the line, the WLR of the sampled liquid is representative of the flow in the line.

Figure 16:
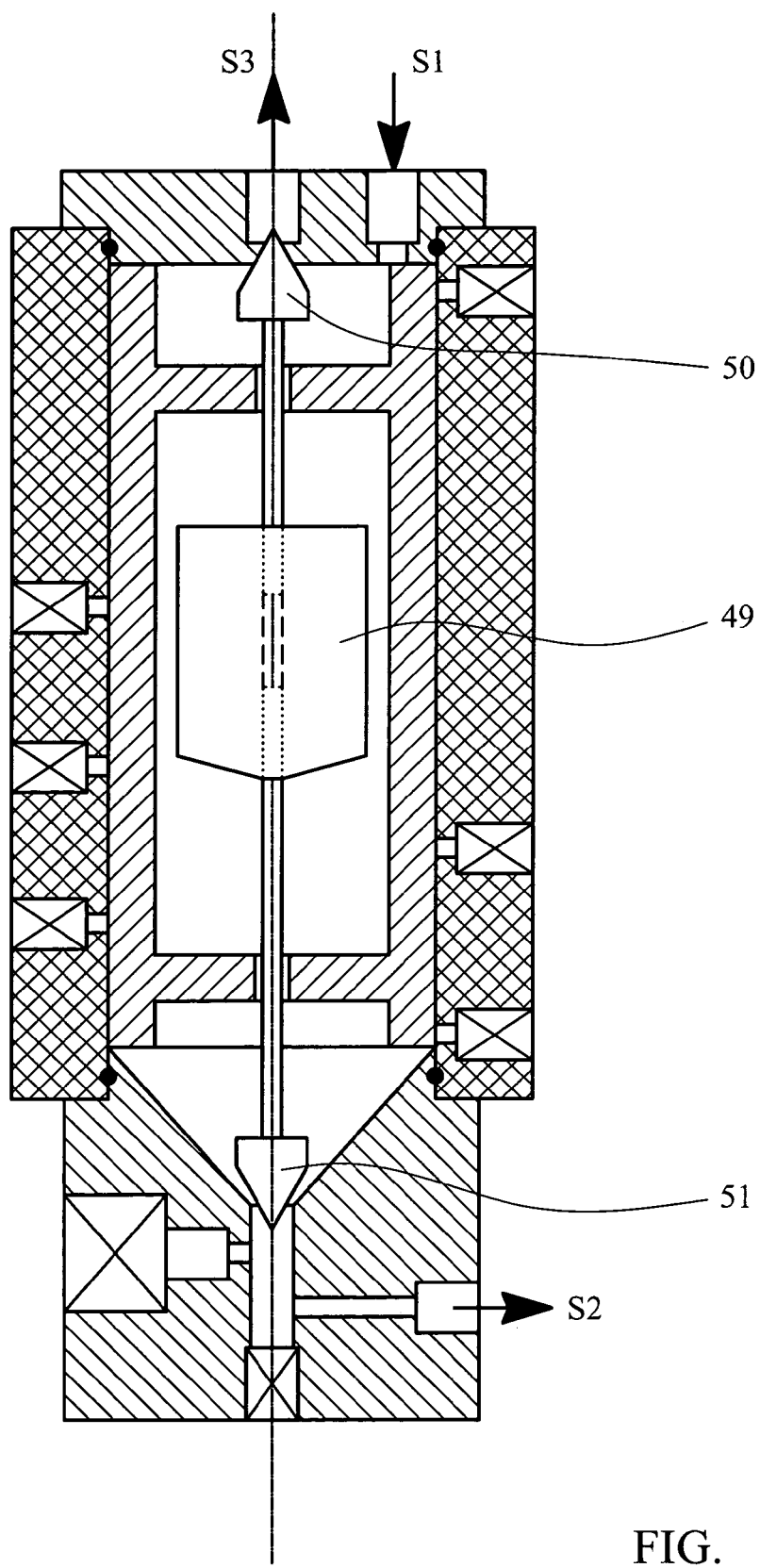
FIG. 16 shows schematic side view of a separator according to an embodiment of the present invention.

Step 2 comprises removing the gas from the sample. This can be done by one of several different ways, but the use of a self regulated mini separator 46 as shown in FIG. 13 and in FIG. 16 is preferred.

Step 3 comprises measuring the WLR of the liquid mixture stream. Several methods exist for evaluating the ratio between oil and water in an oil/water mixture, such as, density, attenuation, optical, and impedance measurement. All of these methods ignore the speed of the fluids and provide only a measurement of the instantaneous volume of each phase. To deduce an accurate measurement of the WLR, the method requires either that both phases flow at the same speed or that a complex slip model be used.

This embodiment of the fluid analysis module provides an accurate measurement of the WLR by forcing both fluids to flow at the same speed. This is done by directing the liquid mixture in a mini channel 47. In such a channel having a diameter of less than 3 to 4 mm, the capillary forces between oil, water and channel walls are creating a train of oil/water slugs which push each other and therefore move at the same speed. From there the WLR can be measured by a WLR measurement device 48 in the mini channel 47 by using known methods. One of these known methods, namely, density measurement using a coriolis meter, is preferred for its robustness and accuracy.

Step 4 comprises re-injecting the full sample, that is, the gas and liquid, into the flow line in a robust way, thus ensuring that there is enough flow and the risks of plugging are minimized. The resulting footprint of the full system of the fluid analysis module of this embodiment is small and does not create big pressure drops in the system. The system, therefore, can be efficiently insulated to avoid thermal variations. These two later points, namely, low pressure and thermal variation, for some hydrocarbons, assist in avoiding formation of deposits (hydrates, asphaltenes, wax, etc.) and avoiding plugging of the system.

Figure 14:
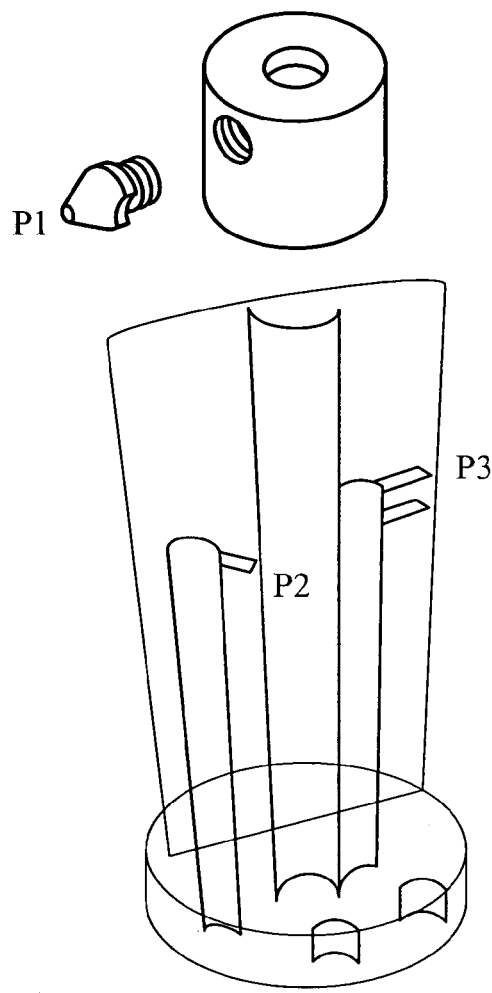
FIG. 14 shows a schematic isometric view of a sampling probe of a fluid analysis according to an embodiment of the present invention.
Figure 15:
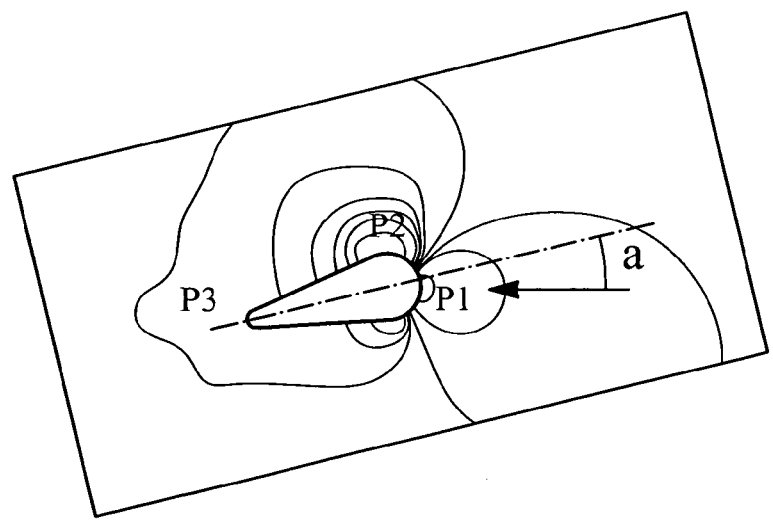
FIG. 15 shows a pressure map of the sampling probe shown in FIG. 14.

Step 1 and step 4 are linked, having an in-port to get the sample and an out-port to return the sample to the flow line. To ensure a flow between the two ports a differential pressure is required between the ports. This can be obtained by several means (pump, venture, etc). The fluid analysis module makes use of an aerofoil type sample probe, as shown in FIG. 14, to create the differential pressure. The position of the ports on the aerofoil is shown as P1, P2, P3 in FIGS. 13 and 14. P1 is the in-port and the out-port is P2 and P3. A simulation of the pressure around the aerofoil mounted with a specific incident angle, a, in respect to the main flow is prepared. FIG. 15 shows the pressure map of this simulation around the probe and from this the pressure differential between the various ports can be deduced. Note that port P1 is mounted in a slightly different way on the simulation than on the arrangement (see 14 and 15). This allows for the adjustment of the angle of the probe, but does not affect the overpressure created by the flow on the port tip.

The specific conical shape of the probe P1 on the arrangement, is made to minimize the catching of debris in the port itself. Any debris hitting the probe on the side will be directed away from the port. This reduces the probability of the debris to get trapped in the port itself. The size of the port is also minimized to avoid big debris from being able to get into the system.

For the out-port, port P2 or P3 can be used. On P2, the pressure is the lowest as indicated on the simulation (15), therefore it will be more efficient to create a flow between P1 and P2. P3 is at a pressure close to the flow line pressure and is used for the gas return.

Suring step 2, the gas separation stage, the multiphase, oil/water/gas (O/W/G) mixture coming from probe P1 enters the mini separator 46 at port S1. In the separator 46 the gas separates from the liquid, exits through port S3 and comes back to the flow line using port P3 of the aerofoil sampling probe. The liquid exits the separator through the lower port S2. Alternative methods of separation such as, for example, a hydro-cyclone could be also used.

For a proper running of the system the liquid level should remain at mid height of the separator 46. To do this a floater system is used as shown in the separator of FIG. 16. If the liquid level is lowered, the floater 49 which is equipped with needle valves 50 and 51 closes port P2 until the liquid rises up the floater 49 and releases the valve. Conversely, in the event of an excess of liquid the floater 49 will raise the upper needle valve 50 to close the gas escape. It will be understood that alternative methods of level control could also be used.

Step 3 is at the WLR measurement device 48, where the liquid mixture exits from the separator 46 from port S2 via mini channel 47, whose diameter is equal to or less than 3 mm. This condition forces the liquids, oil and water, to flow at the same speed and permit an accurate determination of the WLR without using an empirical slip law correction. Various systems such as optical absorption, reflectance, impedance, density measurement can be used to determine the WLR. One of the preferred systems is a mini coriolis meter, which is able to measure the density of the mixture as well as the mass flow rate. From the coriolis density measurement, $r_{coriolis}$, the WLR is simply equal to:

$$WLR = \frac{\rho_{coriolis} - \rho_{oil}}{\rho_{water} - \rho_{oil}}$$

where $r_{water}$ and $r_{oil}$ are the densities of the pure oil and water.

The mass rate measurement may also be calculated and is useful to check that the system is really flowing.

Although the system has been described with reference to its use in the oil and gas industry. The system is not limited to such applications and can be used in any industry where fluid properties are measures, including but not limited to water production, waste water treatment, chemical/petrochemical processing, food processing, pharmaceutical/drug manufacturing, brewing and distilling.

The invention claimed is:

1. A system for analysis of multiphase fluids in real time and at flow line conditions comprising:
    a sampling system for directing a sample fluid stream from a flow line to a fluid analysis module via a sampling port connected to a flow line;
    the fluid analysis module comprising:
        a sensor for measurement of at least one property of the sample fluid stream;
        a processor for processing the measurement data from the sensor;
        communication means for communicating the processed data to a central acquisition unit or computer;

a pre-treatment module for filtering contaminants from the sample fluid stream and for separating the sample fluid stream into single phases; and a post-treatment module to prepare the sample fluid stream for discharge, via the sampling port, by returning the sample fluid stream to its original state before analysis, wherein the fluid analysis module comprises a system integrated into a single unit.

2. The system according to claim 1, further comprising:
a separation module for separating the phases of the sample fluid stream.

3. The system according to claim 1, wherein the fluid analysis module further comprises an array of sensors.

4. The system according to claim 1, further comprising:
a pre-treatment module for removing contaminants from the fluid sample stream.

5. The system according to claim 1, wherein the sensor comprises the processor for processing the measurement data collected from the sensor and comprises communication means for communicating the processed measurement data to the central acquisition unit or computer.

6. The system according to claim 1, wherein the processor is capable of processing measurement data from a plurality of sensors.

7. The system according to claim 6, wherein the communication means comprises a data acquisition module to gather the measurement data generated by each sensor after it has been processed by said processor.

8. The system according to claim 1, wherein the sensor comprises the processor for processing the measurement data collected from the sensor and the communication means communicates processed measurement data from a plurality of sensors.

9. The system according to claim 8, wherein the communication means comprises a computer system configured to further process the gathered measurement data to generate real-time analysis.

10. The system according to claim 1, further comprising:
a fluid sample outlet connected to the fluid analysis module to discharge the sample fluid stream.

11. The system according to claim 10, wherein the fluid sample outlet is in fluid communication with a storage chamber.

12. The system according to claim 10, wherein the fluid sample outlet is in fluid communication with the flow line.

13. The system according to claim 1, further comprising:
a sample device for taking samples for further analysis off-line.

14. The system according to claim 1, wherein the fluid analysis module comprises a fluid sampling device in communication with the flow line, a gas-liquid separator for separating gas from liquids being in communication with the fluid sampling device, and a water to liquid ratio measurement device being in communication with the gas-liquid separator by means of a conduit having a diameter equal to or less than 3 millimeters.

15. The system according to claim 14, wherein the fluid sampling device is used to return a fluid sample to the flow line.

16. The system according to claim 1, wherein measurement of at least one property of the sample fluid stream comprises using chemical agents added to the sample fluid stream to measure the at least one property of the sample fluid stream; and
wherein returning the sample fluid stream to its original state before analysis comprises separating the chemical agents used to measure the at least one property of the sample fluid stream before discharging the sample fluid stream back into the flow line.

17. A method for analysis of a multiphase fluid in real time and at flow line conditions, the method comprising:
obtaining a sample fluid stream from a flow line via a sampling port connected to the flow line;
directing a sample fluid stream to a pre-treatment module for filtering contaminants from the sample fluid stream and for separating the sample fluid stream into single phases;
directing individual phases of the sample fluid stream to a fluid analysis module comprising a sensor for measuring at least one property of the sample fluid stream;
measuring a property of the sample fluid stream using the sensor;
directing the sample fluid stream to a post-treatment module for preparing the sample fluid stream for discharge, via the sampling port, by returning the sample fluid stream to its original state before analysis, wherein the fluid analysis module comprises a system integrated into a single unit, the system comprising the sensor and the post-treatment module.

18. The method according to claim 17, further comprising:
generating real-time fluid property analysis.

19. The method according to claim 18, further comprising:
transmitting the analysis to a remote location.

20. The method according to claim 17, wherein the fluid analysis module comprises an array of sensors, each sensor measuring at least one property of the sample fluid stream.

21. The method according to claim 17, further comprising:
separating the phases of the multiphase fluid into single phase sample fluid stream after obtaining the sample fluid stream from the flow line.

22. The method according to claim 17, further comprising:
separating the phases of the multiphase fluid into single phase sample fluid stream before obtaining the sample fluid stream from the flow line.

23. The method according to claim 17, further comprising:
removing contaminants from the sample fluid stream.

24. The method according to claim 17, further comprising:
discharging the sample fluid stream back into the flow line after measuring a property of the sample fluid stream.

25. The method according to claim 17, further comprising:
storing the sample fluid stream in a container for later treatment or disposal.

26. The method according to claim 17, further comprising:
retaining a sample of the sample fluid stream for further analysis off-line.

27. The method according claim 17, wherein the multiphase fluid is from a hydrocarbon reservoir.

28. The method according to claim 27, further comprising:
separating the multiphase mixture into an oil phase, a water phase, and a gas phase.

29. The method according to claim 17, wherein the fluid analysis module further comprises:
a fluid sampling device in communication with the flow line;

a gas-liquid separator for separating gas from liquids being in communication with the fluid sampling device; and a water to liquid ratio measurement device being in communication with the gas-liquid separator by means of a conduit having a diameter equal to or less than 3 millimeters.

30. The method according to claim 17, further comprising:

adding chemical agents to the sample fluid stream to measure the property of the sample fluid stream; and separating the chemical agents used to measure the property of the sample fluid stream with the pre-treatment module before discharging the sample fluid stream back into the flow line.

31. A fluid analysis module comprising:

a fluid sampling device in communication with a flow line via a sampling port;

a gas-liquid separator for separating gas from liquids being in communication with the fluid sampling device;

a water to liquid ratio measurement device being in communication with the gas-liquid separator by means of a conduit having a diameter equal to or less than 3 millimeters; and a post-treatment module to prepare the sample fluid stream for discharge, via the sampling port, by returning the sample fluid stream to its original state before analysis, wherein the fluid analysis module comprises a system integrated as a single unit.

32. The fluid analysis module according to claim 31, wherein the fluid sampling device is used to return a fluid sample to the flow line.

33. The fluid analysis module according to claim 31, further comprising:

a sensor for measurement of a property of the sample fluid stream using chemical agents added to the sample fluid stream to measure the property of the sample fluid stream; and wherein the post-treatment module separates the chemical agents used to measure the property of the sample fluid stream from the sample fluid stream before discharging the sample fluid stream back into the flow line.

34. A method for analysis of water to liquid ratio of a multiphase fluid in real time and at flow line conditions using a fluid analysis module, the method comprising:

obtaining a fluid sample from a multiphase fluid flow line via a sampling port connected to the flow line;

passing the fluid sample through a liquid-gas separator and separating the gas from the liquid in the sample;

passing the separated liquid through a conduit which connects the liquid-gas separator to a water to liquid measurement device, the conduit having a diameter equal to or less than 3 millimeters;

measuring the water to liquid ratio by means of the water to liquid measurement device; and directing the sample fluid to a post-treatment module for preparing the sample fluid stream for discharge, via the sampling port, by returning the sample fluid stream to its original state before analysis, wherein the fluid analysis module comprises a system integrated as a single unit, the system comprising the liquid-gas separator, the conduit, the water to liquid measurement device, and the post-treatment module.

35. The method of claim 34 further comprising:

directing the sample fluid stream to a fluid analysis module comprising a sensor for measuring at least one property of the sample fluid stream;

measuring a property of the sample fluid stream using a sensor and chemical agents added to the sample fluid stream to measure the property of the sample fluid stream;

separating chemical agents used to measure the property of the sample fluid stream before discharging the sample fluid stream back into the flow line.

* * * * *